United States Patent [19]

Winn et al.

[11] 4,026,894

[45] May 31, 1977

[54] ANTIHYPERTENSIVE AGENTS

[75] Inventors: Martin Winn, Deerfield; Jaroslav Kyncl, Lake Bluff; Daniel Ambrose Dunnigan, Winthrop Harbor; Peter Hadley Jones, Lake Forest, all of Ill.

[73] Assignee: Abbott Laboratories, North Chicago, Ill.

[22] Filed: Oct. 14, 1975

[21] Appl. No.: 621,980

[52] U.S. Cl. .......................... 260/256.4 Q; 424/251
[51] Int. Cl.$^2$ ........................................ C07D 239/84
[58] Field of Search ............ 260/256.4 Q, 256.4 B; 424/251

[56] References Cited

UNITED STATES PATENTS

| | | | |
|---|---|---|---|
| 3,511,836 | 5/1970 | Hess | 260/256.4 Q |
| 3,920,636 | 11/1975 | Takahashi et al. | 260/256.4 Q |

*Primary Examiner*—Paul M. Coughlan, Jr.
*Attorney, Agent, or Firm*—Gildo E. Fato; Robert L. Niblack

[57] ABSTRACT

Described are antihypertensive agents selected from the class consisting of 2[4(tetrahydro-2-furoyl)-piperazino]-4-amino-6,7-dimethoxyquinazoline and 2-[4(tetrahydropyran-2-carbonyl)-piperazinyl]-4-amino-6,7-dimethoxyquinazoline, and pharmaceutically acceptable acid addition salts thereof. The compounds are highly water soluble and can be administered in time release form as well as parenterally, including intravenously.

3 Claims, No Drawings

ANTIHYPERTENSIVE AGENTS

BACKGROUND OF THE INVENTION

A recently introduced drug, 2-[4-(2-furoyl)-1-piperazine-1-y1]-4-amino-6,7-dimethoxyquinazoline, commonly identified by the generic name prazosin, is a hypotensive drug producing peripheral arterial dilation. This drug is represented by the formula:

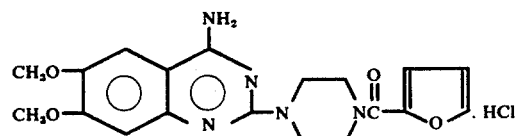

I

This drug however, as reported in The Lancet, May 10, 1975, at page 1095, exhibits significant toxicity and can cause a profound fall in blood pressure. Sudden collapse with loss of consciousness for periods ranging from a few minutes to one hour following use of this drug have been reported. (The Lancet and British Medical Journal, June 28, 1975, pages 727, 728.) The drug prazosin also has a very low solubility and it is therefore postulated that the problem of toxicity sometimes resulting upon oral administration of this drug may be caused by erratic absorption.

SUMMARY OF THE INVENTION

This invention relates to compounds selected from the class consisting of 2[4(tetrahydro-2-furoyl)-piperazino]- 4-amino-6,7-dimethoxyquinazoline and 2-[4(tetrahydropyran-2-carbonyl)piperazinyl]-4-amino-6,7-dimethoxyquinazoline, and pharmaceutically acceptable acid addition salts thereof, represented by the following formulas, respectively.

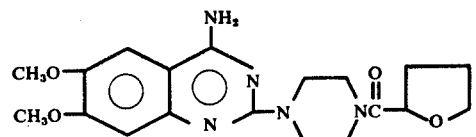

II

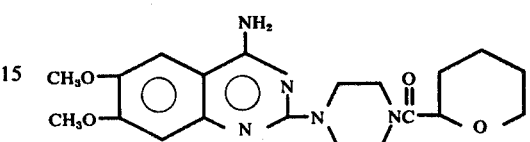

III

The compounds of this invention are useful as antihypertensive agents. They have a solubility of from 100 to about 900 times greater than that of prazosin and are considerably less toxic. Because of their considerable water solubility, these compounds can be administered intravenously, particularly for emergency purposes, and should be absorbed uniformly by all patients. Further, they can be administered in time release form, as well as parenterally, including intravenously.

DETAILED DESCRIPTION

The compounds of the present invention are prepared according to the following reaction scheme:

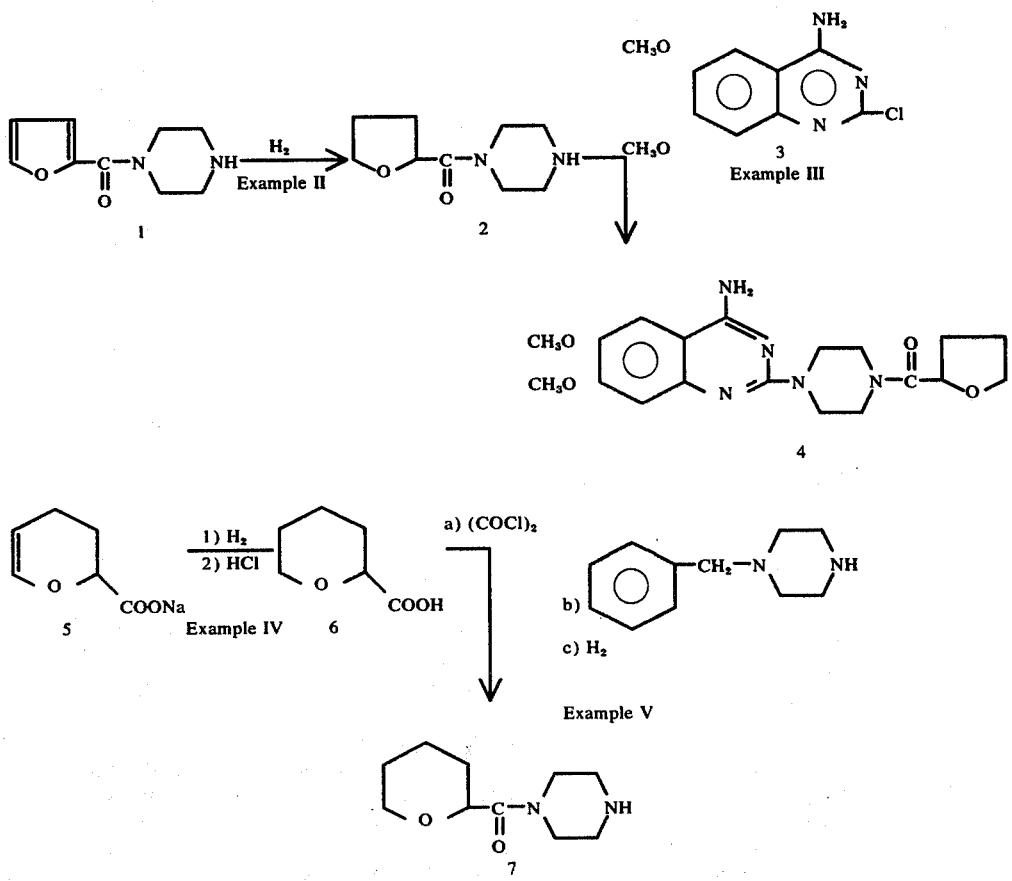

-continued

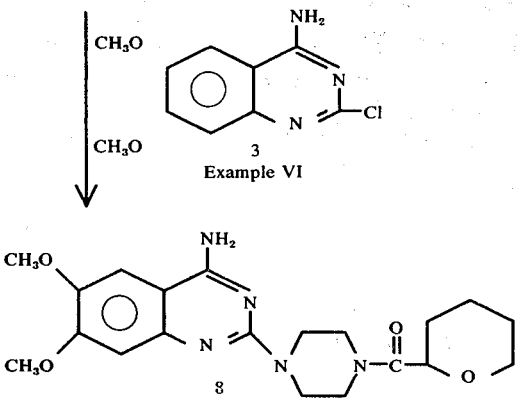
Example VI

In the reactions illustrated above, the compound of formula II is made by hydrogenating the known compound N-(2-furoyl) piperazine to give N(tetrahydro-2-furoyl) piperazine. This compound is reacted with 4-amino-2-chloro-6,7-dimethoxyquinazoline to give the active drug 2-[4-tetrahydro-2-furoyl)piperazinyl ]-4-amino-6,7-dimethoxyquinazoline.

To prepare the compound of formula III, the 3,4-dihydro-2H-pyran-2 carboxylic acid sodium salt is hydrogenated to the tetrahydro-pyran-2-carboxylic acid. This compound converted to the acid chloride with oxalyl chloride and is then treated with N-benzyl piperazine. The resultant N-benzyl-N'-(tetrahydropyran-2-carbonyl)piperazine is hydrogenated to give N-(tetrahydro-pyran-2-carbonyl)piperazine. This compound is reacted with the known compound 4-amino-2-chloro-6,7-dimethoxyquinazoline to give the active drug 2-[-(tetrahydro-pyrran-4-(tetrahydro-pyran-2-carbonyl)piperazinyl]-4-amino-6,7-dimethoxyquinazoline.

The compounds of this invention are useful as antihypertensive agents. The compounds are effective at dosages generally from 0.01 to 100 milligrams daily.

EXAMPLE I

N-(2-Furoyl)Piperazine (1)

This compound and its preparation has been described in Great Britain Patents 1,390,014 and 1,390,015.

194 g. (1 Mole) piperazine hexahydrate was dissolved in 250 ml. $H_2O$. The solution was acidified to pH 4.5 with 6 N HCl. 130.5 g. furoyl chloride (1 Mole) was added along with 10% NaOH solution at such a rate that the pH was maintained at 4.5. After 1 hour, the solution was made basic (pH = 8.5) with NaOH solution. The reaction mixture was continuously extracted with chloroform for 36 hours. The $CHCl_3$ extract was dried over $MgSO_4$ and filtered. Distillation gave 108.2 g. product (60%), b.p. 132°– 138° C/0.6 Mm, m.p. 69°– 70° C.

EXAMPLE II

N-(Tetrahydro-2-Furoyl)Piperazine (2)

The furoyl piperazine of Example I was converted to the hydrobromide salt (m.p. 173°– 175° C.). 39.0 g. of this salt in 250 ml. methyl alcohol and 9.0 g. Raney nickel was hydrogenated at 3 atm. After uptake of $H_2$ ceased, the catalyst was filtered, the solvent concentrated, and the residue crystallized from isopropyl alcohol to give 35.2 g. tetrahydrofuroyl piperazine HBr, m.p. 152°– 156° C. This was suspended in 20 ml. $H_2O$. Then 10.5 g. 50%, NaOH solution was added slowly followed by 2.0 g. solid $Na_2CO_3$. This was extracted with 4–100 ml. portions of warm $CHCl_3$. The $CHCl_3$ extractions were distilled to give 22.5 g. tetrahydrofuroyl piperazine, b.p. 120° – 125° C/0.2 Mm.

EXAMPLE III

2[4-(Tetrahydro-2-Furoyl)Piperazinyl]-4-Amino-6,7-Dimethoxyquinazoline (Hydrochloride (4)

(Hydrochloride of the Compound of Formula II)

To 7.00 g. 2-chloro-4-amino-6,7-dimethoxyquinazoline (3) in 50 ml. methoxyethanol was added 10.8 g. tetrahydrofuroyl piperazine, and the mixture refluxed 3 hours. The clear solution was concentrated and an aqueous solution of potassium bicarbonate was added. The resultant solid that formed was filtered and washed with water. It was then added to methanol and the resulting suspension was acidified with a solution of hydrogen chloride in isopropyl alcohol. The resulting solution was concentrated and the residue crystallized from isopropyl alcohol giving 8.12 g. of product, m.p. 278° – 279° C.

EXAMPLE IV

Tetrahydropyran-2-Carboxylic Acid (6)

210 g. of the sodium salt of 3,4-dihydro-2H-pyran-2-carboxylic acid (5) was dissolved in 2 liters methanol and hydrogenated at 3 atm. pressure over 60 g. Raney nickel catalyst. After hydrogen uptake was complete, the catalyst was filtered and the solvents removed in vacuo. The residue was acidified with concentrated hydrochloric acid and extracted with chloroform. Distillation gave 143.8 g. product, b.p. 75° – 80° C./0.4 Mm, $n^{25} = 1.4623$.

EXAMPLE V

N-(Tetrahydropyran-2-Carbonyl)(7)Piperazine (7)

To 20.5 g. tetrahydropyran-2-carboxylic acid (6) in 50 ml. benzene was added 50 g. oxalyl chloride. The solution was gently heated for 2 hours with vigorous gas evolution. Forty ml. of solvent was distilled through a column at atmospheric pressure. Then 60 ml. fresh benzene was added and 50 ml. solvent was again distilled at atmospheric pressure. The remainder was dissolved in 150 ml. benzene and added slowly to a solution of 27.4 g. N-benzyl piperazine and 17.5 g. triethylamine in 200 ml. benzene, while cooling in an ice bath.

After addition, the mixture was stirred for 1½ hours at room temperature. Then 17 g. sodium carbonate in 100 ml. water was added along with 350 ml. more benzene. The organic phase was separated after stirring, dried over MgSO$_4$, and concentrated. The residue was dissolved in 200 ml ethanol and hydrogenated at 3 atm. over 10.5 g. 5% palladium catalyst. After uptake of hydrogen ceased, the catalyst was filtered and the product isolated by distillation, b.p. 120° – 125° C/0.1 Mm. Solidified to white solid, m.p. 53° – 58° C.

EXAMPLE VI

2-[4(Tetrahydropyran-2-Carbonyl)Piperazinyl]-4-Amino-6,7-Dimethoxyquinazoline Hydrochloride (8)

(Hydrochloride of the compound of formula III)

To 3.00 g. 2-chloro-4-amino-6,7-dimethoxyquinazoline (3) in 20 ml. methoxyethanol was added 5.75 g. 1(tetrahydropyran-2-carbonyl)piperazine (7), and the mixture was refluxed three hours. The mixture was cooled and the solid filtered and washed with isopropyl alcohol, giving 2.50 g. product as the HCl salt. The filtrate was concentrated in vacuo and the residue treated with potassium bicarbonate in water yielding a solid, m.p. 134° – 136° C. (Base of product). This was converted to the hydrochloride by suspending the methanol and treating with HCl in isopropyl alcohol. Total yield of hydrochloride was 4.30 g., m.p. 305° C. decomp.

The solubility of the compounds of formulas II and III were found to be considerably greater than the prior art compound, prazosin HCl (compound of formula I). The solubility of prazosin HCl was measured by stirring 368.5 mg. of the compound in 25 ml. of water, permitting it to remain overnight at room temperature and then filtering. The water in the filtrate was removed in vacuo and the residue weighed and found to be 16.7 mg. The solubility of prazosin HCl was consequently calculated as 0.67 mg./ml. of water.

The solubility of the hydrochloride salt of the compound of formula II was measured by weighing 91.4 mg. into a vial and adding water dropwise with stirring until a clear solution was formed and then weighing again. The weight of water required to dissolve 91.4 mg. of the compound was found to be 0.163 g. The solubility of the compound of formula II was calculated as 590 mg. per ml. of water. The ratio of solubility in comparison to the compound of formula I is 880.

Likewise, the solubility of the hydrochloride salt of the compound of formula III was found to be 56.5 mg. per ml. of water or about 100 times that of the compound of formula I.

The advantageous solubility of the compounds of formulas II and III facilitate their preparation into oral dosage and parenteral forms for human administration and more importantly, permit administration intravenously. As discussed in *Dispensing Of Medication*, Eric W. Martin, Editor, 7th edition, 1975, injections provide the most direct route for achieving the effect of a drug within the human body. By planned formulation of the dosage form, combined with an appropriate choice of one of the injection routes, it is possible to vary the effect of a drug from an almost instantaneous onset with a few minutes duration to be delayed onset of several hours and a prolonged duration up to several weeks. This versatility of therapeutic effect makes the injection of therapeutic agents a very valuable route of administration. It is also noted that since the transport systems of the human body are aqueous in nature, medications to be injected should normally be in an aqueous system and when the product is immiscible with water, it must be limited to such routes of administration as intramuscular and subcutaneous. The article further notes that while suspensions and emulsions may be used, most parenteral products are preferably prepared as solutions.

It is therefore apparent that being highly soluble in water, the compounds described herein can readily be adopted for parenteral administration and moreover, can be used in hypertensive crises which generally require intravenous administration for rapid onset of action.

The antihypertensive effect of the hydrochloride salts of the compounds of formulas II and III were screened in spontaneously hypertensive (SH) rats and found to be potent antihypertensive agents. The screening is conducted as follows:

Male spontaneously hypertensive (SH) rats are trained to be restrained in a wire mesh cylinder in a warming box, at least two training cycles being conducted before testing. The rats are warmed for about 1/2 hour period to blood pressure measurement, the warming box being maintained at a constant temperature of 36° C.

An occluding cuff attached to the programed sphymomanometer is placed near the base of the tail of each rat and the pressure in the cuff is increased automatically from 0 to 250 milimeters of mercury (mm H$_g$) at a rate of 1 mm H$_g$ per second. The total time for each cycle of inflation and deflation of the cuff is 50 seconds and the interval between cycles is one minute.

A photocell is placed distal to the cuff to record the pulses due to forward motion of blood flow with each heart beat. As the pressure in the cuff increases, the pulse disappears completely at a point where cuff pressure equals or exceeds the arterial blood pressure and it reappears during deflation at approximately the same pressure. Five interference free signals for deflation are recorded for each rat. Rats with a blood pressure of 180 mm H$_g$ or more during the control period are used in the study. Blood pressure and heart rate readings are recorded on a model VII Grass polygraph at intervals of 1, 3, 5 and 24 hours after administration of the drug.

The data obtained is summarized in the following tables from which it is apparent that the compounds of formula II and III are potent antihypertensive agents which lower the blood pressure of spontaneously hypertensive rats without causing any significant changes in heart rate.

As an example, the hydrochloride of the compound of formula II produced a decrease in blood pressure of the magnitude of between 20 and 60% when administered intraperitoneally in the dose range from 0.3 – 30 mg./kg. The duration of the effect was greater than 24 hours at the dose of 30 mg./kg. while the lowest dose of 0.3 mg./kg. still caused an effect lasting for more than five hours. Likewise, when administered via the oral route, the compound caused a fall in blood pressure by up to approximately 40% when administered at doses of 3 and 10 mg./kg.

TABLE 1

ANTIHYPERTENSIVE EFFECT OF THE HYDROCHLORIDE SALT OF THE COMPOUND OF FORMULA II,

TABLE 1-continued

ORALLY ADMINISTERED IN SH RATS

| ORAL DOSE (mg/kg) | N | | CONTROL BLOOD PRESSURE (mm Hg) | HEART RATE (beats/min) | PERCENT CHANGE AT: | | | | | | | |
|---|---|---|---|---|---|---|---|---|---|---|---|---|
| | | | | | 1 HOUR | | 3 HOURS | | 5 HOURS | | 24 HOURS | |
| | | | | | BP | HR | BP | HR | BP | HR | BP | HR |
| 30 | 4 | Mean | 224.5 | 365.0 | −30.0 | −9.8 | −23.8 | −8.8 | −26.0 | −15.5 | −4.0 | −8.0 |
| | | S.E.M. | ±1.9 | ±26.3 | ±2.1 | ±5.9 | ±1.7 | ±5.1 | ±1.8 | ±5.9 | ±1.1 | ±8.7 |
| 10 | 4 | Mean | 227.5 | 355.0 | −37.0 | 12.3 | −42.0 | 16.5 | −38.0 | −10.3 | −12.0 | 1.5 |
| | | S.E.M. | ±4.8 | ±26.3 | ±2.5 | ±10.5 | ±4.1 | ±13.0 | ±1.8 | ±12.7 | ±2.6 | ±7.9 |
| 3 | 4 | Mean | 227.0 | 395.0 | −29.0 | −9.3 | −33.3 | −11.0 | −31.5 | −11.0 | −12.3 | −5.3 |
| | | S.E.M. | ±5.3 | ±23.6 | ±2.3 | ±9.2 | ±0.6 | ±7.7 | ±4.6 | ±7.6 | ±4.1 | ±8.3 |
| 1 | 4 | Mean | 211.8 | 375.0 | −15.8 | −9.0 | −17.3 | −9.3 | −22.5 | −8.5 | 3.5 | −4.5 |
| | | S.E.M. | ±8.4 | ±29.9 | ±3.5 | ±1.8 | ±3.7 | ±11.1 | ±5.3 | ±11.5 | ±3.6 | ±4.5 |
| 0.3 | 4 | Mean | 203.5 | 325.0 | −15.8 | −1.0 | −22.8 | −2.8 | −21.3 | −2.8 | 2.0 | 10.5 |
| | | S.E.M. | ±9.5 | ±28.7 | ±5.6 | ±7.2 | ±3.1 | ±18.0 | ±1.8 | ±1.6 | ±4.2 | ±10.0 |
| 0.1 | 4 | Mean | 204.3 | 350.0 | 3.8 | 3.0 | 1.8 | 4.8 | −7.3 | −6.8 | −1.5 | −0.3 |
| | | S.E.M. | ±4.9 | ±20.8 | ±2.4 | ±3.9 | ±4.3 | ±3.1 | ±2.2 | ±3.9 | ±1.5 | ±6.7 |
| 0.03 | 4 | Mean | 230.3 | 350.0 | −5.3 | −4.3 | −1.8 | −8.5 | −9.3 | −14.5 | −3.3 | −8.8 |
| | | S.E.M. | ±6.2 | ±5.8 | ±3.6 | ±4.4 | ±2.6 | ±5.1 | ±2.7 | ±4.9 | ±3.9 | ±5.6 |

| INTRA-PERITONEAL DOSE (mg/kg) | N | | CONTROL BLOOD PRESSURE (mm Hg) | HEART RATE (beats/min) | PERCENT CHANGE AT: | | | | | | | |
|---|---|---|---|---|---|---|---|---|---|---|---|---|
| | | | | | 1 HOUR | | 3 HOURS | | 5 HOURS | | 24 HOURS | |
| | | | | | BP | HR | BP | HR | BP | HR | BP | HR |
| 30 | 4 | Mean | 193.5 | 410.0 | −59.5 | −9.0 | −42.3 | 1.8 | −44.5 | 5.3 | −22.3 | 5.8 |
| | | S.E.M. | ±3.5 | ±19.1 | ±4.1 | ±7.8 | ±9.5 | ±6.7 | ±6.9 | ±8.2 | ±11.8 | ±6.5 |
| 10 | 4 | Mean | 207.3 | 355.0 | −49.8 | 9.0 | −41.5 | 24.5 | −41.8 | 34.5 | −7.5 | 14.0 |
| | | S.E.M. | ±7.4 | ±15.0 | ±6.4 | ±3.0 | ±7.2 | ±6.7 | ±3.8 | ±6.9 | ±3.4 | ±9.7 |
| 3 | 4 | Mean | 201.8 | 405.0 | −45.3 | 7.8 | −39.0 | −1.5 | −40.0 | 3.0 | −2.3 | −0.5 |
| | | S.E.M. | ±4.3 | ±33.0 | ±2.0 | ±12.4 | ±1.8 | ±5.8 | ±4.1 | ±7.5 | ±3.2 | ±9.1 |
| 1 | 4 | Mean | 198.5 | 370.0 | −26.5 | 22.8 | −27.5 | 2.8 | −17.0 | 11.5 | 3.8 | −9.5 |
| | | S.E.M. | ±3.6 | ±10.0 | ±7.7 | ±4.3 | ±0.6 | ±3.7 | ±4.9 | ±8.5 | ±2.1 | ±1.2 |
| 0.3 | 4 | Mean | 205.8 | 320.0 | −22.3 | 20.0 | −26.5 | 10.3 | −20.5 | 14.3 | 2.5 | 10.0 |
| | | S.E.M. | ±4.4 | ±8.2 | ±6.8 | ±11.2 | ±2.1 | ±8.3 | ±4.1 | ±6.6 | ±4.3 | ±7.8 |

TABLE 2

ANTIHYPERTENSIVE EFFECT OF THE COMPOUND OF FORMULA I, ORALLY ADMINISTERED IN SH RATS

| ORAL DOSE (mg/kg) | N | | CONTROL BLOOD PRESSURE (mm Hg) | HEART RATE (beats/min) | PERCENT CHANGE AT: | | | | | | | |
|---|---|---|---|---|---|---|---|---|---|---|---|---|
| | | | | | 1 HOUR | | 3 HOURS | | 5 HOURS | | 24 HOURS | |
| | | | | | BP | HR | BP | HR | BP | HR | BP | HR |
| 30 | 4 | Mean | 232.5 | 335.0 | −34.0 | −3.8 | −31.3 | −11.5 | −29.3 | −14.8 | −14.5 | −1.5 |
| | | S.E.M. | ±4.8 | ±9.6 | ±2.0 | ±10.7 | ±3.3 | ±8.9 | ±2.7 | ±6.8 | ±3.6 | ±1.5 |
| 10 | 4 | Mean | 212.5 | 300.0 | −23.8 | 3.0 | −22.3 | 12.3 | −22.0 | −0.8 | −2.3 | 23.3 |
| | | S.E.M. | ±5.8 | ±18.3 | ±0.6 | ±7.8 | ±2.6 | ±4.7 | ±5.1 | ±6.9 | ±3.5 | ±5.8 |
| 3 | 4 | Mean | 207.5 | 360.0 | −19.3 | 0.5 | −19.8 | 11.5 | −20.5 | 1.5 | 5.3 | 6.0 |
| | | S.E.M. | ±2.4 | ±23.1 | ±3.2 | ±12.0 | ±2.3 | ±17.9 | ±2.4 | ±17.7 | ±3.4 | ±5.7 |
| 1 | 4 | Mean | 226.8 | 325.0 | −31.8 | 2.0 | −17.8 | 6.8 | −19.5 | −1.0 | −2.3 | 10.0 |
| | | S.E.M. | ±8.9 | ±26.3 | ±2.8 | ±4.9 | ±2.6 | ±10.7 | ±2.4 | ±10.8 | ±3.5 | ±8.1 |
| 0.3 | 4 | Mean | 217.0 | 390.0 | −32.8 | −5.5 | −33.8 | −5.0 | −30.0 | −13.8 | −12.3 | 3.0 |
| | | S.E.M. | ±5.8 | ±40.4 | ±1.3 | ±8.8 | ±1.0 | ±8.6 | ±2.3 | ±4.8 | ±2.7 | ±3.7 |
| 0.1 | 4 | Mean | 205.5 | 305.0 | −9.8 | 13.5 | −17.5 | 18.3 | −22.8 | 1.5 | −1.3 | 3.5 |
| | | S.E.M. | ±5.7 | ±17.1 | ±3.1 | ±4.9 | ±0.6 | ±3.0 | ±3.4 | ±9.9 | ±1.4 | ±8.5 |
| 0.03 | 4 | Mean | 221.3 | 390.0 | −4.5 | 4.8 | −0.8 | −9.3 | −11.5 | −9.8 | 1.3 | −2.0 |
| | | S.E.M. | ±9.5 | ±38.7 | ±2.2 | ±12.1 | ±4.2 | ±8.8 | ±2.7 | ±10.3 | ±3.9 | ±6.9 |

| INTRA-PERITONEAL DOSE (mg/kg) | N | | CONTROL BLOOD PRESSURE (mm Hg) | HEART RATE (beats/min) | PERCENT CHANGE AT: | | | | | | | |
|---|---|---|---|---|---|---|---|---|---|---|---|---|
| | | | | | 1 HOUR | | 3 HOURS | | 5 HOURS | | 24 HOURS | |
| | | | | | BP | HR | BP | HR | BP | HR | BP | HR |
| 30 | 4 | Mean | 211.3 | 375.0 | −43.3 | −1.8 | −48.5 | 4.8 | −55.5 | 3.5 | −24.5 | −6.5 |
| | | S.E.M. | ±6.1 | ±12.6 | ±2.8 | ±5.8 | ±5.0 | ±7.7 | ±2.2 | ±8.8 | ±6.1 | ±4.2 |
| 10 | 4 | Mean | 201.8 | 360.0 | −41.0 | 5.8 | −34.0 | 14.8 | −27.0 | 7.3 | −13.0 | −7.5 |
| | | S.E.M. | ±3.5 | ±29.4 | ±9.7 | ±8.0 | ±3.8 | ±14.5 | ±5.4 | ±9.3 | ±4.5 | ±5.7 |
| 3 | 4 | Mean | 194.3 | 405.0 | −45.0 | 0.3 | −31.5 | −6.5 | −26.3 | −17.0 | −2.3 | −4.0 |
| | | S.E.M. | ±6.5 | ±23.6 | ±4.4 | ±3.3 | ±3.5 | ±8.6 | ±2.7 | ±6.8 | ±3.8 | ±8.8 |
| 1 | 4 | Mean | 201.3 | 365.0 | −20.0 | 2.8 | −15.3 | 1.8 | −13.5 | 10.5 | 3.5 | 12.8 |
| | | S.E.M. | ±5.5 | ±42.7 | ±5.9 | ±6.0 | ±3.7 | ±5.6 | ±4.8 | ±14.4 | ±1.0 | ±5.5 |
| 0.3 | 4 | Mean | 207.0 | 410.0 | −20.8 | −2.5 | −18.3 | −0.5 | −13.8 | −12.0 | −4.3 | −5.0 |
| | | S.E.M. | ±1.3 | ±31.1 | ±8.2 | ±2.5 | ±4.3 | ±5.1 | ±2.0 | ±6.2 | ±1.6 | ±5.4 |

TABLE 3

ANTIHYPERTENSIVE EFFECT OF THE HYDROCHLORIDE SALT OF THE COMPOUND OF FORMULA III IN SH RATS

| | Percent Change (2 Rats) At: | | | |
|---|---|---|---|---|
| | 1 Hour | 3 Hours | 5 Hours | 24 Hours |
| Oral Dose 1 mg./kg. Intraperitoneal Administration, | −34,−30 | −25,−26 | −21,−18 | −7,−3. |
| 30 mg./kg. | −58,−50 | −71,−76 | −47,−53 | −28,−36 |

The acute, intravenous toxicity in mice of the compound of Formula II in comparison to that of Formula I is summarized in Table 4.

TABLE 4

INTRAVENOUS TOXICITY IN MICE (MALE AND FEMALE)

$LD_{50}$ IN MG./KG.

(95% Confidence Limits)

|  | COMPOUND OF FORMULA I | HYDROCHLORIDE OF COMPOUND OF FORMULA II |
|---|---|---|
| Injected Immediately After Formulation (A) | 97.8 (93.7–102.6) | 259.3** (251.9–267.6) |
| Injected 24 Hours After Formulation (B) | 46.6* (44.5–49.3) | 252.9 (245.2–262.4) |

*Significant difference between A and B; $p \leq 0.05$
**Significant difference between compounds; $p \leq 0.05$ From this data, it is apparent that the hydrochloride of the compound of Formula II exhibits significantly lower toxicity than the compound of Formula I when administered within twenty minutes following preparation of the solution or suspension, respectively. The difference in toxicities is even more significant when both compounds are injected 24 hours after preparation of the formulation.

The compounds of this invention can be formulated into various pharmaceutically acceptable dosage forms such as tablets, capsules, pills, and the like, for immediate or sustained release by combining the active compound with suitable pharmaceutically acceptable carriers or diluents according to methods well known in the art. Such dosage forms may include excipients, binders, fillers, flavoring and sweetening agents, and other therapeutically inert ingredients necessary in the formulation of the desired preparation. Preparations for parenteral administration generally include sterile aqueous or nonaqueous solutions, suspensions or emulsions.

What is claimed is:

1. A compound selected from the group consisting of 2-[4(tetrahydro-2-furoyl)-piperazino]-4-amino-6,7-dimethoxyquinazoline and 2-[4(tetrahydropyran-2-carbonyl)piperazinyl]-4-amino-6,7-dimethoxyquinazoline and pharmaceutically acceptable acid addition salts thereof.

2. A compound in accordance with Claim 1: 2-[4(tetrahydro-2-furoyl)-piperazino]-4-amino-6,7-dimethoxyquinazoline hydrochloride.

3. A compound in accordance with Claim 1: 2-[4(tetrahydropyran-2-carbonyl)piperazinyl]-4-amino-6,7-dimethoxyquinazoline hydrochloride.

* * * * *